(12) United States Patent
Tajima et al.

(10) Patent No.: US 12,402,943 B1
(45) Date of Patent: Sep. 2, 2025

(54) MEDICAL DEVICE

(71) Applicant: ALIVAS INC., Tokyo (JP)

(72) Inventors: Tomoyuki Tajima, Tokyo (JP); Shohei Matsuhara, Tokyo (JP); Yoshiki Watabe, Tokyo (JP); Pisit Kiatkittikul, Tokyo (JP); Keisuke Matsumoto, Tokyo (JP)

(73) Assignee: ALIVAS INC., Tokyo (JP)

( * ) Notice: Subject to any disclaimer, the term of this patent is extended or adjusted under 35 U.S.C. 154(b) by 0 days.

(21) Appl. No.: 18/865,719

(22) PCT Filed: Apr. 16, 2024

(86) PCT No.: PCT/JP2024/015097
§ 371 (c)(1),
(2) Date: Nov. 14, 2024

(51) Int. Cl.
*A61B 18/18* (2006.01)
*A61B 18/00* (2006.01)

(52) U.S. Cl.
CPC ............ *A61B 18/1815* (2013.01); *A61B 2018/00023* (2013.01); *A61B 2018/00077* (2013.01);
(Continued)

(58) Field of Classification Search
CPC ..... A61B 18/1815; A61B 18/08; A61B 18/12; A61B 18/042; A61B 18/1487; A61B 18/1492; A61B 18/18; A61B 18/1402; A61B 2018/00994; A61B 2018/1475; A61B 2018/1846; A61B 2018/1861; A61B 2018/1465; A61B 2018/147; A61B 2018/1472; A61B 2018/00023; A61B 2018/00011; A61B 2018/00029; A61B 2018/0016; A61B 2018/00273;
(Continued)

(56) References Cited

U.S. PATENT DOCUMENTS 6,010,500 A * 1/2000 Sherman ............ A61B 18/1492
606/49
11,266,425 B2 * 3/2022 McCaffrey ....... A61B 17/22022
(Continued)

FOREIGN PATENT DOCUMENTS

CN 102743225 A 10/2012
CN 102908188 A 2/2013
(Continued)

OTHER PUBLICATIONS

International Search Report and Written Opinion of the International Searching Authority, mailed on Jun. 4, 2024, issued for the corresponding International Application No. PCT/JP2024/015097, 20 pages, with English translation.
(Continued)

*Primary Examiner* — Thomas A Giuliani
(74) *Attorney, Agent, or Firm* — LUCAS & MERCANTI, LLP

(57) ABSTRACT

A medical device includes a liquid circulation unit that enables transfer of a liquid (a perfusion liquid) supplied from a port unit of a second hub of an energy application device to a distal end portion of a first shaft of a catheter device. The energy application device is relatively movable forward and backward with respect to the catheter device so that an energy application unit can be disposed at a predetermined position on the distal end side of the first shaft.

8 Claims, 10 Drawing Sheets

(52) U.S. Cl.
CPC ........... *A61B 2018/00178* (2013.01); *A61B 2018/00184* (2013.01); *A61B 2018/00345* (2013.01); *A61B 2018/00577* (2013.01); *A61B 2018/1861* (2013.01)

(58) Field of Classification Search
CPC .......... A61B 2018/00279; A61B 2018/00285; A61B 2018/00077; A61B 2018/00178; A61B 2018/00345; A61B 2018/00577; A61B 2018/00404; A61B 2018/1435
USPC ......... 606/27–29, 33, 37–42, 45–49; 607/98, 607/99, 101, 104, 105, 113, 115, 116
See application file for complete search history.

(56) References Cited

U.S. PATENT DOCUMENTS

| | | | | |
|---|---|---|---|---|
| 2003/0114844 | A1* | 6/2003 | Ormsby | A61B 18/1492 607/156 |
| 2012/0259326 | A1* | 10/2012 | Brannan | A61B 18/1815 606/33 |
| 2014/0031812 | A1 | 1/2014 | Brannan et al. | |
| 2014/0066915 | A1* | 3/2014 | Zhou | A61B 18/18 606/41 |
| 2021/0401497 | A1* | 12/2021 | Tajima | A61B 18/1815 |
| 2022/0126062 | A1 | 4/2022 | Warnking | |

FOREIGN PATENT DOCUMENTS

| | | |
|---|---|---|
| JP | 2014-516615 A | 7/2014 |
| JP | 2017-196461 A | 11/2017 |
| JP | 2021-168985 A | 10/2021 |

OTHER PUBLICATIONS

Notice of Refusal, dated Jan. 28, 2025, issued for the corresponding Japanese Patent Application No. 2024-568179, 6 pages, with English translation.

* cited by examiner

MEDICAL DEVICE

CROSS REFERENCE TO RELATED APPLICATION

This Application is a 371 of PCT/JP2024/015097 filed on Apr. 16, 2024, which is incorporated herein by reference.

TECHNICAL FIELD

The present invention relates to a medical device.

BACKGROUND ART

There are medical devices known for being used to emit energy in a living organ of a human body to treat and alleviate various diseases and the like. As a treatment method using such a medical device, a procedure for ablating nerves present outside a blood vessel (nerve ablation) is performed.

In a medical device that is used in the above procedure, various kinds of energy can be adopted as the energy to be applied to the treatment target site. As an example of such a medical device, there is a device that adopts the structure of a catheter device that applies thermal energy directly or indirectly to the nerve to be treated from the vicinity of a distal end (see Patent Literature 1, for example).

CITATION LIST

Patent Literature

Patent Literature 1: JP 2017-196461 A

SUMMARY OF INVENTION

Technical Problem

In the catheter device disclosed in Patent Literature 1, energy is emitted from an energy application unit (an ultrasonic radiation source) in a state where the distal end portion of a catheter is disposed at a predetermined position in a blood vessel. When treatment is performed, there is a distance between the energy application unit and the inner wall of the blood vessel, and therefore, it is necessary to radiate energy with high power. Furthermore, when energy is emitted from the energy application unit with high power, the energy application unit and the electric transmission path (a conductive unit) disposed in the catheter may generate heat and have a high temperature. Therefore, the catheter device is required to include a structure for cooling the energy emitting unit with a perfusion liquid.

The present invention has been made in view of the above problems, and aims to provide a medical device that ablates nerves present outside a blood vessel, and is capable of cooling an energy application unit and a conductive unit disposed in a first shaft of a catheter device with a perfusion liquid during treatment.

Solution to Problem

The present invention can be achieved with any one of the following means (1) to (9).

(1)

A medical device including:
a catheter device that includes:
a first shaft that is configured to be insertable into a blood vessel and has one or more opening formed at a distal end portion; and
a first hub disposed at a proximal end portion of the first shaft;
an energy application device that includes:
an energy application unit configured to apply energy to a surrounding nerve outside the blood vessel, the energy being for ablating the surrounding nerve running in parallel with the blood vessel;
a second hub in which an electrical connector unit that supplies electrical energy to the energy application unit is disposed, the second hub including a port unit for inwardly supplying a predetermined liquid;
a conductive unit that has an elongated shape and connects the electrical connector unit and the energy application unit; and
a second shaft that extends from the second hub to a side of the energy application unit, accommodates at least part of a proximal end side of the conductive unit, and is inserted into the first hub; and
a liquid circulation unit that allows the liquid supplied from the port unit to be sent to the distal end portion of the first shaft, in which
the energy application device is relatively movable forward and backward with respect to the catheter device, so that the energy application unit can be placed at a predetermined position on the distal end side of the first shaft.

(2)

The medical device according to (1), in which the liquid circulation unit is a fluid communication passage that includes the port unit of the second hub, an internal space of the second hub, a lumen of the second shaft, an internal space of the first hub, and a lumen of the first shaft.

(3)

The medical device according to (1) or (2), in which the second shaft is inserted into the first hub, to allow a distal end portion of the second shaft to move between a first position defined in the first hub and a second position defined closer to a proximal end side in the first hub than the first position, and
the liquid circulation unit is provided in both a state where the distal end portion of the second shaft is located at the first position and a state where the distal end portion of the second shaft is located at the second position.

(4)

The medical device according to any one of (1) to (3), in which
the first shaft includes:
a first opening formed at a distal end; and
a plurality of second openings that is located on a proximal end side of the first opening and is open toward a lateral side of the first shaft.

(5)

The medical device according to (4), in which the plurality of second openings is open in a direction not to face an inner wall of the blood vessel in a state where the first shaft is inserted in the blood vessel.

(6)

The medical device according to (5), in which
the distal end portion of the first shaft includes:
a curved portion that has a shape curved with respect to a predetermined first reference axis; and
a linear portion that is located on a proximal end side of the curved portion, and extends substantially linearly along a second reference axis extending in a direction intersecting with the first reference axis.

(7)

The medical device according to (6), in which the curved portion is a spiral portion that extends spirally around the first reference axis.

(8)

The medical device according to (6) or (7), in which the first shaft includes:
a first portion provided at a position including the curved portion;
a second portion that is located on a proximal end side of the first portion, and is provided with the plurality of second openings; and
a third portion that is located on a proximal end side of the second portion, and is provided at a position including the linear portion, and
an inner diameter of the second portion and the third portion is larger than an inner diameter of the first portion.

(9)

The medical device according to any one of (1) to (8), in which the energy application unit is capable of emitting a microwave or an ultrasonic wave as the energy.

Advantageous Effects of Invention

With the medical device according to (1), it is possible to ablate, outside a blood vessel, a surrounding nerve extending in parallel with the blood vessel, by causing energy emission from the energy application unit disposed in the first shaft of the catheter device. Also, the medical device according to (1) includes the liquid circulation unit that enables transfer of the liquid (perfusion liquid) supplied from the port unit of the second hub of the energy application device to the distal end portion of the first shaft. Thus, during treatment, the surgeon can cool the energy application unit and the conductive unit disposed in the first shaft of the catheter device with the perfusion liquid.

DESCRIPTION OF EMBODIMENTS

Figure 1:
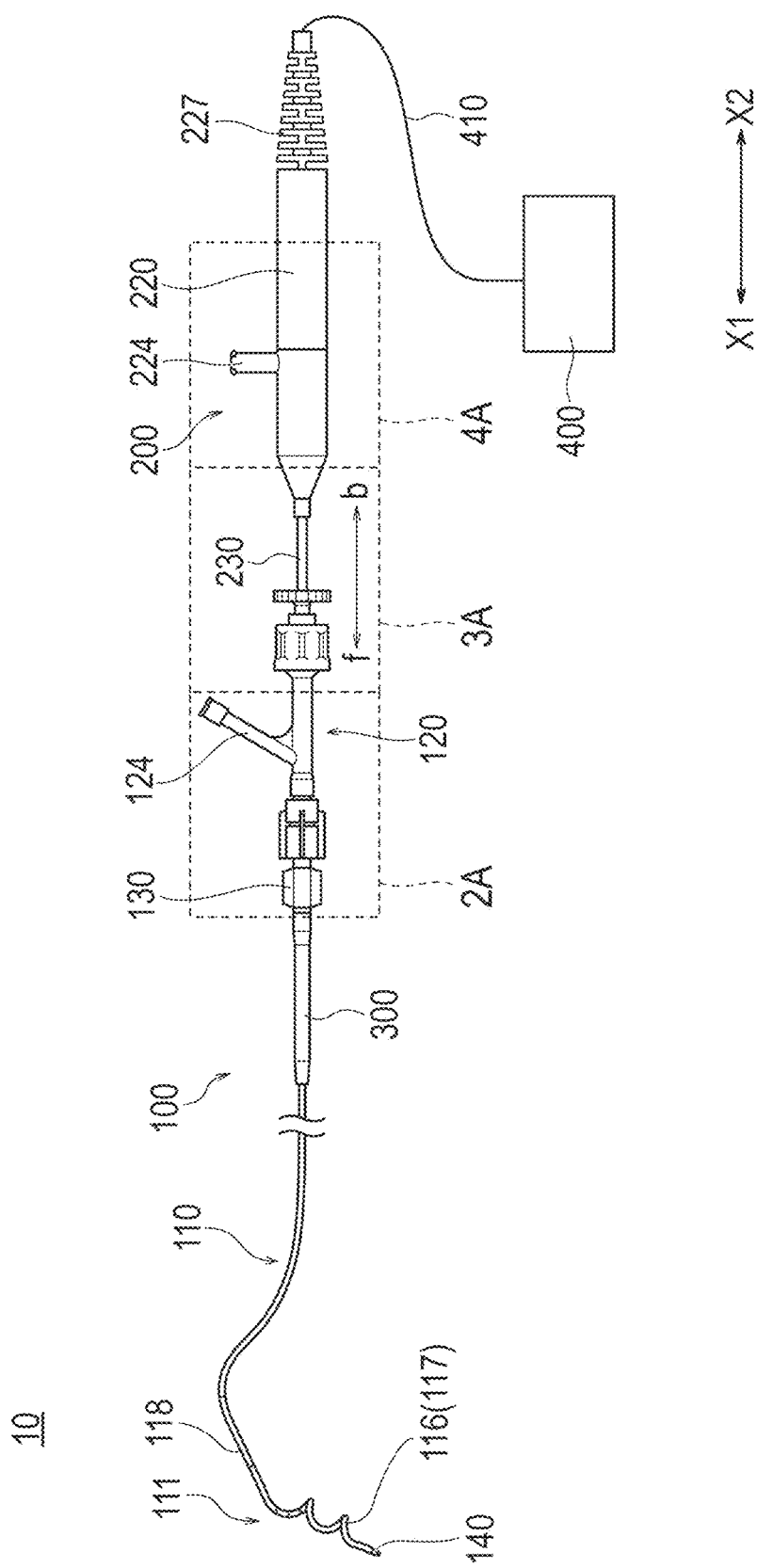
FIG. 1 is a diagram schematically illustrating an overall configuration of a medical device according to an embodiment.

In the description below, embodiments of the present invention will be explained with reference to the accompanying drawings. Note that the following description does not limit the technical scope of the claims or the meanings of terms used in the claims. Also, dimensional ratios in the drawings are exaggerated for ease of explanation, and may differ from actual ratios. Further, a numerical range "X to Y" in the present specification means "not smaller than X and not greater than Y".

Figure 12:
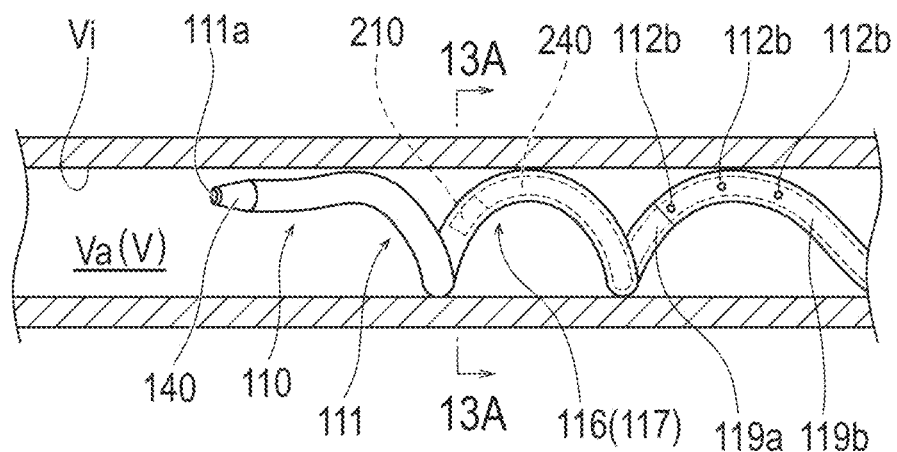
FIG. 12 is a schematic cross-sectional view (a longitudinal sectional view in the extending direction of a blood vessel) for explaining an example of use of the medical device.
Figure 13:
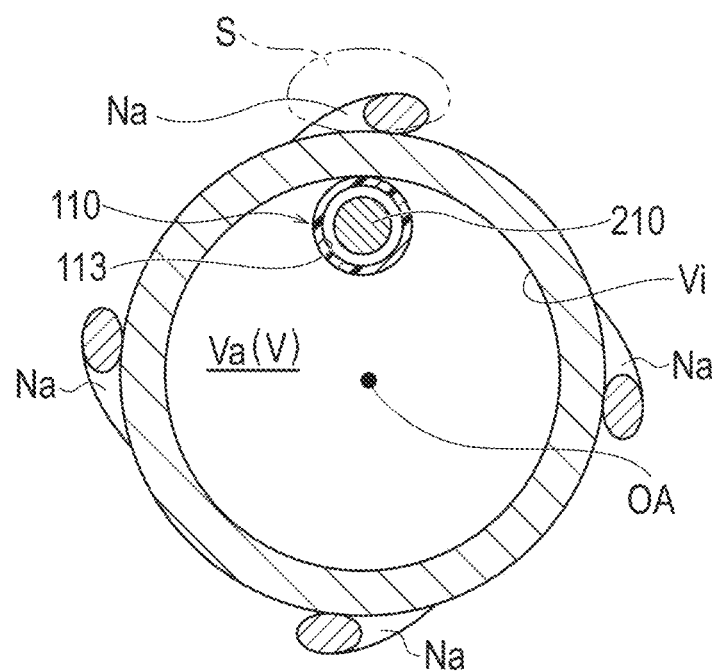
FIG. 13 is a cross-sectional view (a transverse sectional view) of a portion indicated by arrows 13A-13A in FIG. 12.

FIGS. 1 to 11 are diagrams for explaining the respective components of a medical device 10 according to an embodiment. FIGS. 12 and 13 are diagrams for explaining examples of use of the medical device 10. Note that FIG. 12 is a longitudinal sectional view in the extending direction of a blood vessel V to be treated, and FIG. 13 is a transverse sectional view of the blood vessel V to be treated (a transverse sectional view of a portion indicated by an arrow 13A-13A in FIG. 12).

As illustrated in FIGS. 12 and 13, in a procedure using the medical device 10, the surgeon (a medical worker such as a medical doctor) can enhance peristaltic movement of the intestinal tract by performing a treatment for reducing the activity of the autonomic nerves in the blood vessel V having surrounding nerves (extravascular nerves) Na that innervate the intestinal tract of the patient. By performing such a treatment, the surgeon can facilitate alleviation of at least one symptom among abdominal distension, abdominal pain, perineal discomfort, and frequent defecation caused by constipation and/or an abnormality in peristaltic movement of the intestinal tract of the patient (at least one symptom among the symptom groups caused by alleviation of constipation and/or an abnormality in peristaltic movement of the intestinal tract of the patient).

The blood vessel V to which the treatment method is applied is not limited to any particular kind, as long as the peristaltic movement of the intestinal tract of the patient can be enhanced by a predetermined treatment (denervation by application of energy, for example) according to the embodiment. As an example of the blood vessel V, at least one blood vessel can be suitably selected from among the superior mesenteric artery Va, the celiac artery, and the inferior mesenteric artery. In particular, the superior mesenteric artery Va can be selected as the blood vessel V from the viewpoint of more effectively enhancing the peristaltic movement of the intestinal tract after the treatment. In the present embodiment, an example in which treatment is performed on the superior mesenteric artery Va will be described (see FIGS. 12 and 13).

As the treatment according to the embodiment, the surgeon applies energy to one surrounding nerve Na (or a plurality of surrounding nerves) that is present outside the blood vessel V and extends in parallel with the blood vessel V. By applying energy to the surrounding nerve Na and impairing the surrounding nerve Na, the surgeon completely or partially blocks autonomic nerve transmission to the digestive tract from the surrounding nerve Na. By performing such treatment, the surgeon can enhance peristaltic movement of the intestinal tract.

The following mechanisms are considered as the reasons why peristaltic movement of the intestinal tract is activated by performing the above treatment.

When the surrounding nerve Na is impaired by the energy applied through the inside of the blood vessel V, and the autonomic nerve transmission to the digestive tract by the surrounding nerve Na is completely or partially blocked, the sympathetic nervous system weakens relatively and the parasympathetic nervous system becomes dominant between the sympathetic nervous system and the parasympathetic nervous system. Also, when neurotransmission from the central nerves is blocked, the intestinal nervous system that autonomously controls intestinal movement in the periphery becomes dominant, and peristaltic movement of the intestinal tract becomes active. Further, as peristaltic movement of the intestinal tract becomes active, the colon transit time is accelerated and normalized, and thus, alleviation of at least one symptom among abdominal distension, abdominal pain, perineal discomfort, and frequent defecation caused by constipation and/or an abnormality in peristaltic movement of the intestinal tract is facilitated.

In particular, by the treatment method according to the present embodiment, it is possible to suitably accelerate alleviation of a symptom of constipation of a colon transit time delay type that is derived from degradation in intestinal peristaltic movement of the large intestine and a delay observed in the stool transit time in functional constipation without an organic abnormality in the colon.

The treatment target site (a region including one or a plurality of surrounding nerves Na illustrated in FIG. 13) S of the treatment using the medical device 10 is not limited to any particular site, as long as it is possible to enhance peristaltic movement of the intestinal tract. For example, in the blood vessel V, the treatment may be performed on any appropriate range (site) in the running direction (extending direction) of the blood vessel V, or the treatment may be performed on any appropriate range (site) in a circumferential direction (a circumferential direction of the transverse cross-section) of the blood vessel V. Also, the treatment may be performed a plurality of times at a plurality of appropriate portions of the same blood vessel V, or may be performed a plurality of times at any appropriate portions of a plurality of different blood vessels V.

In the present embodiment, a treatment method that regards the superior mesenteric artery Va as the blood vessel V to be treated as described above will be described.

The treatment method includes performing treatment on a site around the origin of the superior mesenteric artery Va. Specifically, the treatment target site S preferably includes a range of 0 mm to 20 mm in the extending direction of the superior mesenteric artery Va, with reference to the opening of the superior mesenteric artery Va (an opening connected to the aorta), for example. By applying energy within the above range of the superior mesenteric artery Va, it is possible to effectively suppress energy transmission to organs (such as the pancreas or the duodenum, for example) located on the peripheral side of the superior mesenteric artery Va.

Also, from the viewpoint of more reliably suppressing energy transmission to the organs located on the peripheral side of the superior mesenteric artery Va, it is still more preferable to apply energy from the superior mesenteric artery Va only within the range of 0 mm to 20 mm in the extending direction of the superior mesenteric artery Va, for example.

The invasion depth of the energy from an energy application unit 210 disposed in the superior mesenteric artery Va toward the outside of the blood vessel V preferably includes a range of 1 mm to 6 mm from the intima of the superior mesenteric artery Va, for example. The surrounding nerves Na present outside the superior mesenteric artery Va are present at relatively deep positions around the origin of the superior mesenteric artery Va. More specifically, the surrounding nerves Na exist in a bundle while being supported by connective tissue in adipose tissue outside the superior mesenteric artery Va. Accordingly, in a case where energy is applied from around the origin of the superior mesenteric artery Va, the surrounding nerves Na around the superior mesenteric artery Va can be efficiently denervated by causing the energy to reach a position of 1 mm to 6 mm of the intima of the superior mesenteric artery Va.

Next, the medical device 10 according to the present embodiment is described.

<Medical Device 10>

As illustrated in FIGS. 1 to 4, the medical device 10 includes a catheter device 100, an energy application device 200, and a liquid circulation unit 50.

As illustrated in FIGS. 1 to 4, 12, and 13, the catheter device 100 includes a first shaft 110 that is configured to be insertable into the blood vessel V and has one or more openings 112a and 112b formed at a distal end portion 111, and a first hub 120 disposed at a proximal end portion 113 of the first shaft 110.

Also, the energy application device 200 includes: the energy application unit 210 that is configured to be able to apply energy for ablating the surrounding nerve Na that is located outside the blood vessel V and extends in parallel with the blood vessel V; a second hub 220 in which an electrical connector unit 240 for supplying electrical energy to the energy application unit 210 is disposed, and a port unit 224 for supplying a predetermined liquid to the inside is included; an elongated conductive unit 260 that connects the electrical connector unit 240 and the energy application unit 210; and a second shaft 230 that extends from the second hub 220 toward the energy application unit 210, accommodates at least part of the proximal end side of the conductive unit 260, and is inserted into the first hub 120.

In the description of the present specification, the side of the first shaft 110 of the catheter device 100 to be inserted into the blood vessel V (the side indicated by an arrow X1) is defined as the distal end side, and the side of the energy application device 200 that is located on the opposite side to the distal end side and is the side on which the second hub 220 is disposed (the side indicated by an arrow X2) is defined as the proximal end side.

<Catheter Device 100>

Figure 2:
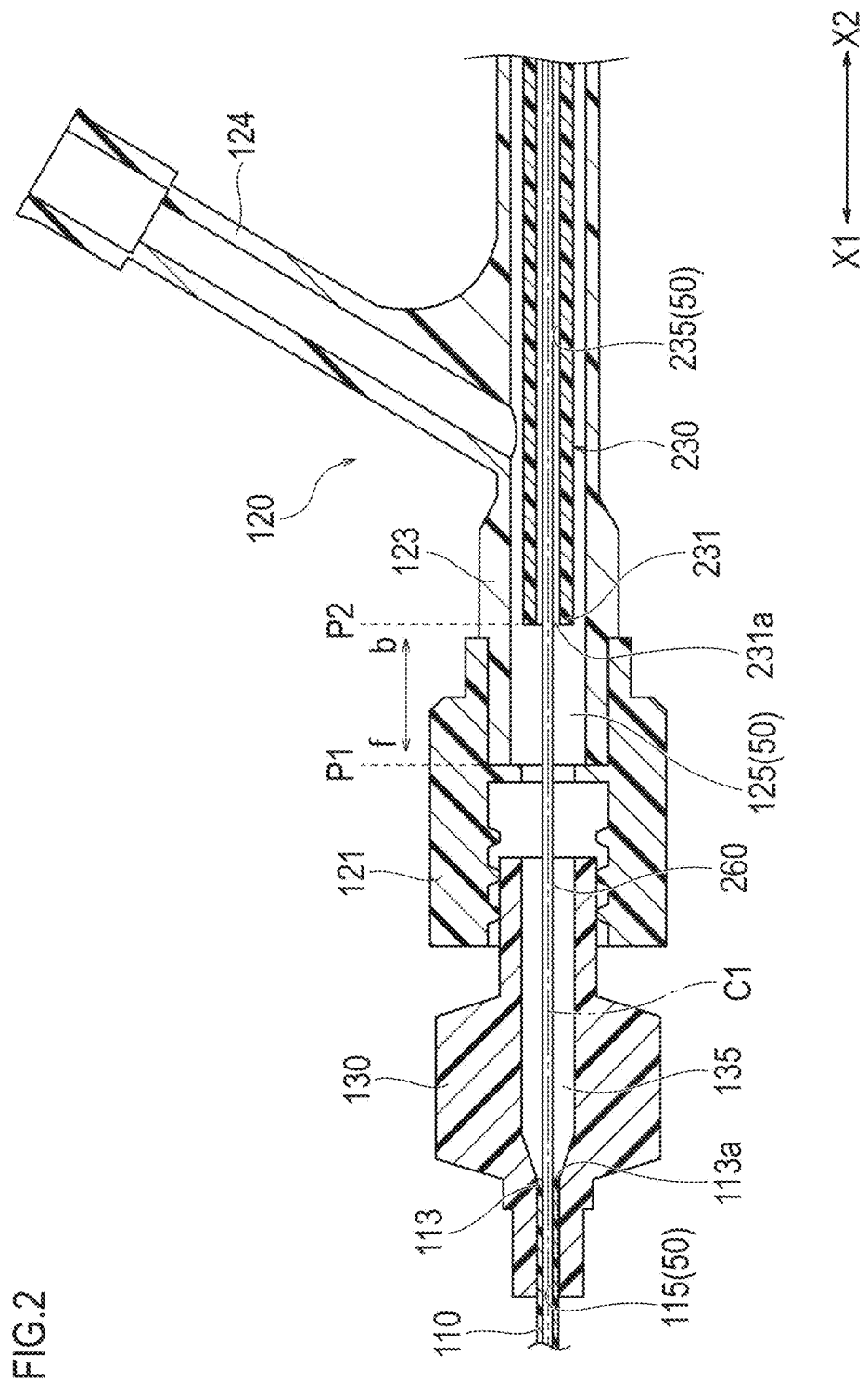
FIG. 2 is an enlarged cross-sectional view of a portion indicated as a dashed-line portion 2A in FIG. 1.
Figure 7:
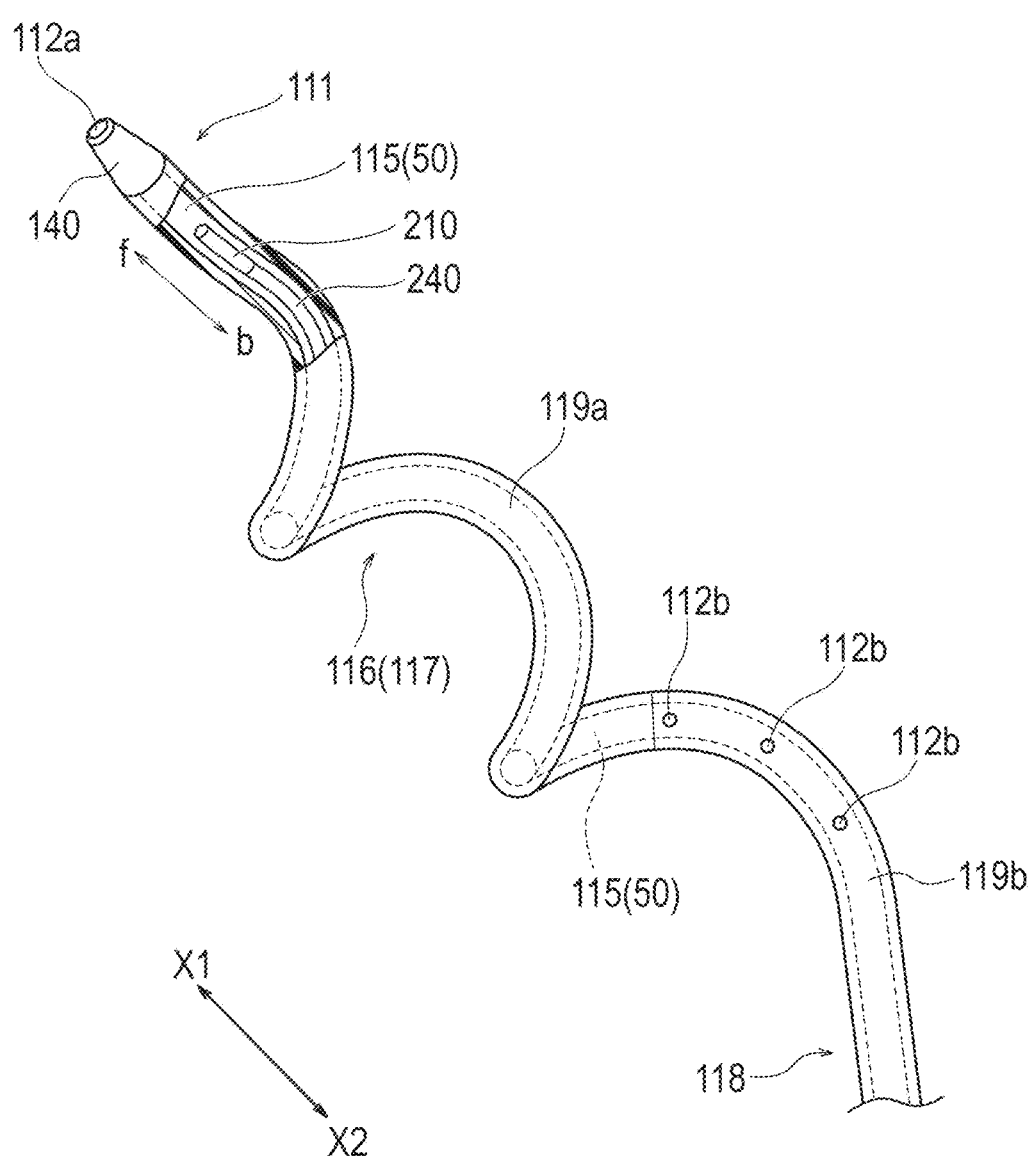
FIG. 7 is a partial cross-sectional view of the vicinity of the distal end portion of the first shaft.

As illustrated in FIGS. 1, 2, and 7, the first shaft 110 included in the catheter device 100 can be formed with a tubular member having a lumen 115 formed therein.

Figure 5:
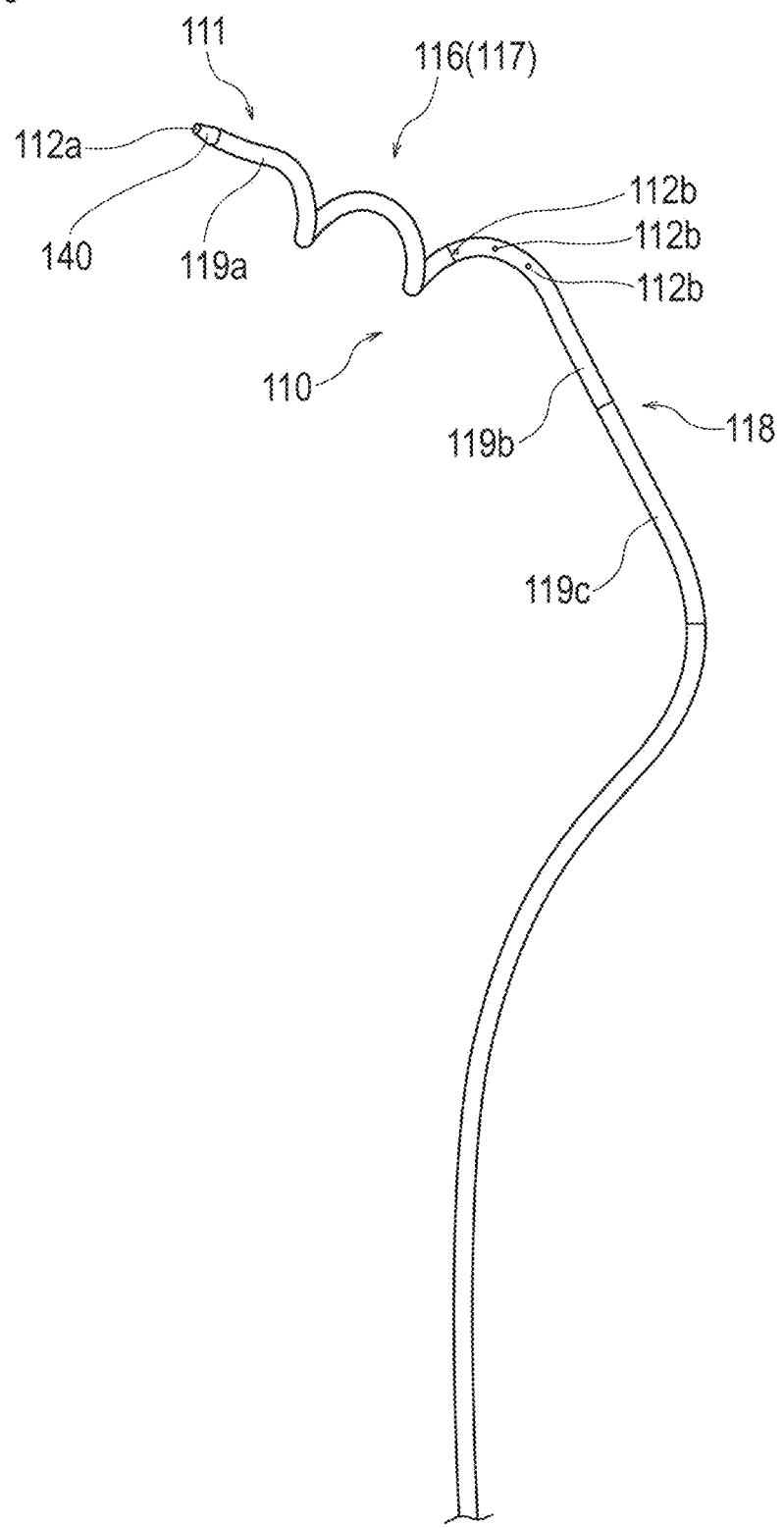
FIG. 5 is an enlarged perspective view of a portion of a first shaft.
Figure 6:
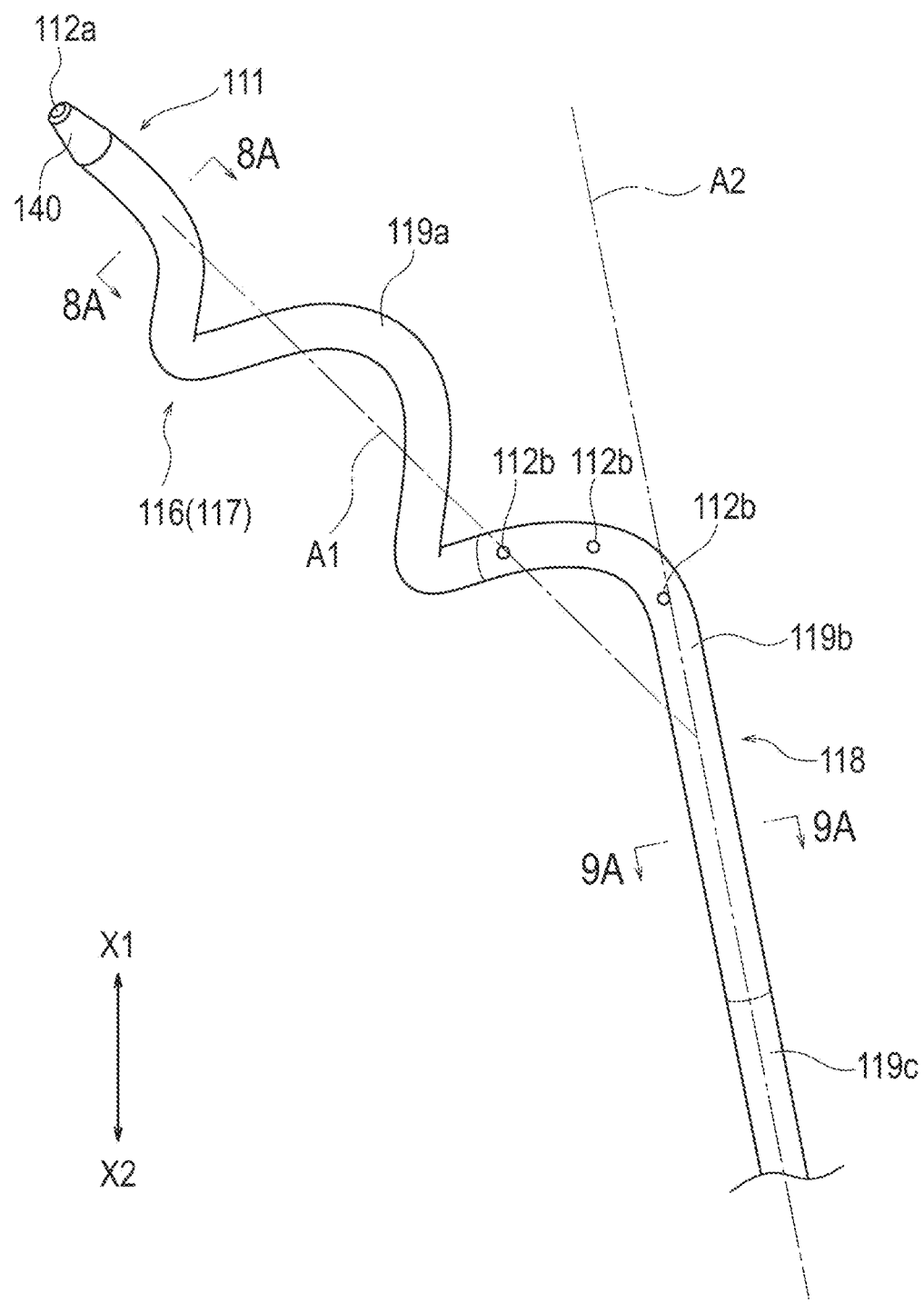
FIG. 6 is an enlarged perspective view of the vicinity of a distal end portion of the first shaft.

As illustrated in FIGS. 5, 6, and 7, the first shaft 110 has a first opening 112a formed at the distal end, and a plurality of second openings (side holes) 112b that is located on the proximal end side of the first opening 112a and is open toward the lateral side of the first shaft 110.

The catheter device 100 can supply a contrast medium to the lumen 115 of the first shaft 110 via a port unit 124 of the first hub 120. The contrast medium supplied to the lumen 115 of the first shaft 110 can be discharged to the outside of the first shaft 110 through the plurality of second openings 112*b* and the first opening 112*a*.

The energy application device 200 can supply liquid (saline, for example) to a lumen 235 of the second shaft 230 via the port unit 224 of the second hub 220. As described later, the lumen 235 of the second shaft 230 communicates with the lumen 115 of the first shaft 110 via the first hub 120. Therefore, the liquid supplied via the port unit 224 of the second hub 220 can be sent into the lumen 115 of the first shaft 110, and be discharged to the outside of the first shaft 110 via the plurality of second openings 112*b* and the first opening 112*a* of the first shaft 110.

As illustrated in FIGS. 6 and 7, the first shaft 110 includes a distal end tip 140 formed with a flexible resin material. The distal end tip 140 has the first opening 112*a* that communicates with the lumen 115 of the first shaft 110. The first opening 112*a* forms a distal end opening that faces the distal end side of the first shaft 110.

Note that the first shaft 110 does not necessarily include the distal end tip 140. In a case where the first shaft 110 does not include the distal end tip 140, the first opening 112*a* can be formed with an opening provided at the distal end of the first shaft 110.

As illustrated in FIG. 6, the distal end portion 111 of the first shaft 110 includes: a curved portion 116 having a curved shape with respect to a predetermined first reference axis A1; and a linear portion 118 that is located on the proximal end side of the curved portion 116 and extends substantially linearly along a second reference axis A2 extending in a direction intersecting with the first reference axis A1.

As the first shaft 110 includes the curved portion 116, at least part of the distal end portion 111 of the first shaft 110 can be disposed so as to come into contact with an inner wall Vi of the blood vessel V when the distal end portion 111 of the first shaft 110 is inserted into the blood vessel V (see FIGS. 12 and 13). In a state where at least part of the distal end portion 111 of the first shaft 110 is in contact with the inner wall Vi of the blood vessel V, the surgeon causes the energy application unit 210 disposed in the lumen 115 of the distal end portion 111 of the first shaft 110 to emit energy, so that energy can be efficiently transmitted to the surrounding nerve Na located outside the blood vessel V.

Further, as the first shaft 110 has the linear portion 118 disposed on the proximal end side with respect to the curved portion 116, the first shaft 110 can be disposed so that a position on the proximal end side with respect to the curved portion 116 comes into contact with the upper end of the blood vessel V (the upper end around the origin from the aorta to the superior mesenteric artery Va, for example) when the first shaft 110 is inserted into the blood vessel V. By placing the linear portion 118 of the first shaft 110 so as to come into contact with the inner wall Vi of the blood vessel V of the blood vessel V, the surgeon can cause the linear portion 118 to firmly support the first shaft 110 with respect to the blood vessel V, and prevent the curved portion 116 from being displaced.

As illustrated in FIG. 6, the curved portion 116 can be formed with a spiral portion 117 extending spirally around the first reference axis A1, for example.

In the catheter device 100, the curved portion 116 is formed with the spiral portion 117. Therefore, when the first shaft 110 is inserted into the blood vessel V, the spiral portion 117 extends spirally in the blood vessel V, and comes into contact with the inner wall Vi of the blood vessel V in a continuous state in a predetermined range. Accordingly, as illustrated in FIG. 12, the portion at which the spiral portion 117 is formed can be continuously brought into contact with the inner wall Vi of the blood vessel V. As a result, in the catheter device 100, the energy application unit 210 can be disposed at any desired portion in the extending direction of the blood vessel V and the circumferential direction of the blood vessel V within the range in which the spiral portion 117 is formed. Thus, energy can be easily and efficiently applied to the surrounding nerve Na from a position close to the inner wall Vi of the blood vessel V.

A specific shape (such as the pitch of the spiral, the number of turns, the outer diameter of the spiral, and the winding direction of the spiral, for example) of the spiral portion 117 is not limited to any particular shape, as long as any desired portion of the spiral portion 117 can be brought into contact with the inner wall Vi of the blood vessel V when the first shaft 110 is disposed in the blood vessel V.

Also, the curved portion 116 is not limited only to a shape like that of the spiral portion 117, as long as at least part of the distal end portion 111 of the first shaft 110 can be brought into contact with the inner wall Vi of the blood vessel V. The curved portion 116 can also be configured to have a shape curved in a zigzag form with respect to the first reference axis A1, a circular shape intersecting with the first reference axis A1, an elliptical shape, a rectangular shape, a U-shape folded back from the distal end side to the proximal end side, or the like, for example.

As illustrated in FIG. 12, the plurality of second openings 112*b* is open in a direction not to face the inner wall Vi of the blood vessel V in a state where the first shaft 110 is inserted in the blood vessel V. Note that the direction in which the plurality of second openings 112*b* are open can be defined as a direction in which the first reference axis A1 serving as a reference for the spiral shape of the spiral portion 117 is oriented inward (see FIG. 6).

The plurality of second openings 112*b* is located at a second portion 119*b* on the proximal end side of the spiral portion 117. In the present embodiment, each of the second openings 112*b* is formed with a circular hole. Further, three second openings 112*b* are arranged at predetermined intervals so as to be disposed at different positions in the extending direction of the first shaft 110. The opening area of each of the second openings 112*b* is smaller than the opening area of the first opening 112*a*.

Since each opening of the plurality of second openings 112*b* is open in a direction not to face the inner wall Vi of the blood vessel V, it is possible to prevent the second openings 112*b* from being blocked by the inner wall Vi of the blood vessel V when the first shaft 110 is inserted into the blood vessel V. Furthermore, the plurality of second openings 112*b* is disposed at predetermined positions on the proximal end side away from the first opening 112*a* located at the distal end of the first shaft 110. Accordingly, even when the distal end side of the first shaft 110 is inserted to a portion at which the cross-sectional area on the back side of the blood vessel V is narrowed, it is possible to image the portion on the proximal side of the blood vessel V, by causing each of the second openings 112*b* to discharge the contrast medium.

Note that the number, the placement locations, the shape, the opening area, and the like of the second openings 112*b* are not limited to any particular kinds, as long as the contrast medium can be discharged from a position on the proximal end side of the first opening 112*a*.

As illustrated in FIGS. 5, 6, and 7, the first shaft 110 includes: a first portion 119*a* provided at a position including the curved portion 116; the second portion 119*b* that is located on the proximal end side of the first portion 119*a*, and has the plurality of second openings 112*b* formed therein; and a third portion 119c that is located on the proximal end side of the second portion 119b, and is provided at a position including the linear portion 118.

Figure 8:
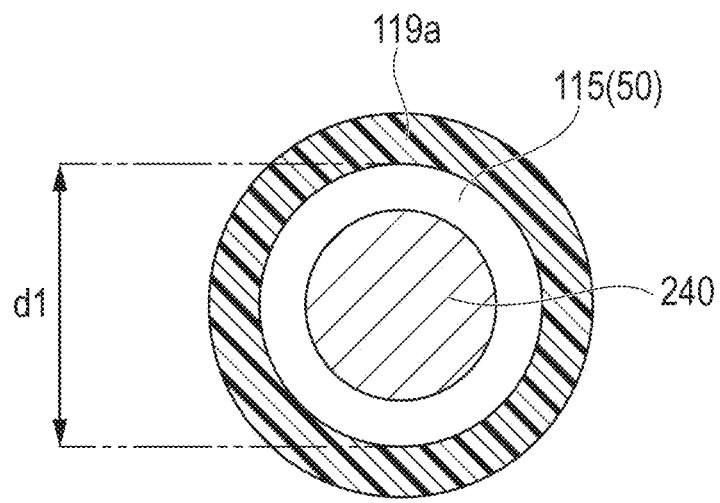
FIG. 8 is a cross-sectional view (a transverse sectional view) of a portion indicated by arrows 8A-8A in FIG. 6.
Figure 9:
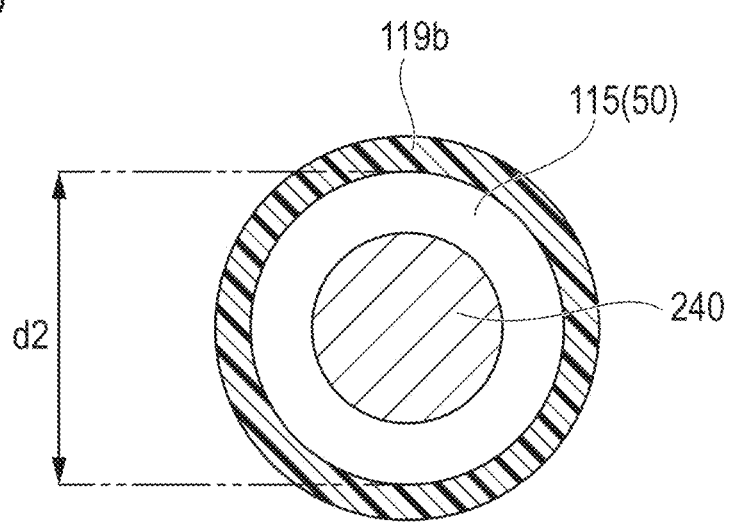
FIG. 9 is a cross-sectional view (a transverse sectional view) of a portion indicated by arrows 9A-9A in FIG. 6.

As illustrated in FIGS. 8 and 9, the inner diameter d2 of the second portion 119b and the third portion 119c can be configured to be larger than the inner diameter d1 of the first portion 119a. Although FIG. 9 shows an axis-orthogonal cross-sectional view of the second portion 119b, the third portion 119c is also configured to have a cross-sectional shape (with the inner diameter d2 or the like) substantially similar to that of the second portion 119b in the present embodiment.

In the first shaft 110, the inner diameter of the first portion 119a provided in a predetermined range from the distal end to the proximal end side of the first shaft 110 is relatively small. Thus, it is possible to prevent the energy application unit 210 from being disposed at a position shifted radially outward from the center position on an axis-orthogonal cross-section of the lumen 115 at a portion corresponding to the first portion 119a of the lumen 115. For example, if the energy application unit 210 is disposed at a position largely shifted radially outward from the center position as described above at a time of treatment, there is a possibility that a deviation in intensity distribution of the energy emitted from the energy application unit 210 or a deviation in resonance (in a case where the energy application unit 210 is formed with an antenna element) will occur. With the first shaft 110 including the first portion 119a, it is possible to prevent the occurrence of such a problem in advance.

Further, in the first shaft 110, the inner diameters of the second portion 119b and the third portion 119c located on the proximal end side of the first portion 119a are relatively large. Thus, it is possible to ensure large clearances for the lumen 115 at the portions corresponding to the respective portions 119b and 119c. Accordingly, flows of the contrast medium and the perfusion liquid in the respective portions 119b and 119c can be made smooth, and the contrast medium and the perfusion liquid can be more reliably discharged from the second openings 112b formed in the second portion 119b.

As illustrated in FIGS. 8 and 9, the portion of the first shaft 110 corresponding to the first portion 119a can be configured to have a tube wall thickness smaller than that of the portions of the first shaft 110 corresponding to the second portion 119b and the third portion 119c. Thus, in the first shaft 110, the inner diameter d2 of each of the portions 119b and 119c can be configured to be larger than the inner diameter d1 of the first portion 119a.

Note that the first portion 119a can be configured to have a higher flexibility than the second portion 119b and the third portion 119c. With such a configuration, in the first shaft 110, the flexibility of the first portion 119a in which the curved portion 116 is formed is high, and the rigidity of each of the portions 119b and 119c located on the proximal end side of the first portion 119a is high. Accordingly, the first shaft 110 having a high supporting force capable of supporting the contact of the curved portion 116 with the inner wall Vi of the blood vessel V at each of the portions 119b and 119c on the proximal end side of the curved portion 116 while preventing the inner wall Vi of the blood vessel V from being damaged by the curved portion 116 configured so that at least a portion thereof comes into contact with the inner wall Vi of the blood vessel V is formed. The magnitude relationship in terms of flexibility can be adjusted with the types of the materials forming the respective portions 119a, 119b, and 119c of the first shaft 110, for example.

As illustrated in FIG. 6, part of the distal end side of the second portion 119b can be configured to have a predetermined curved shape between the linear portion 118 and the curved portion 116. Also, this portion can be configured to have a curved shape with a larger curvature radius than that of the spiral portion 117, for example. As the second portion 119b has a portion with a relatively large curvature radius as described above, it is possible to prevent the flows of the contrast medium and the perfusion liquid from being stagnant in the second portion 119b. Thus, the contrast medium and the perfusion liquid can be more smoothly discharged from the second openings 112b formed in the second portion 119b.

Note that the portion of the first shaft 110 extending to the proximal end side of the third portion 119c can be configured to have substantially the same cross-sectional shape (the inner diameter or the like) as the third portion 119c.

The first shaft 110 can be formed with a resin material that is known in the catheter field, for example. Also, the first shaft 110 may be formed with a single-layer or multilayer resin tube member, or may have a blade wire or the like embedded therein to reinforce its rigidity. Further, the outer surface of the first shaft 110 may be coated with a hydrophilic coating or the like. These aspects also apply to the second shaft 230 described later.

Figure 3:
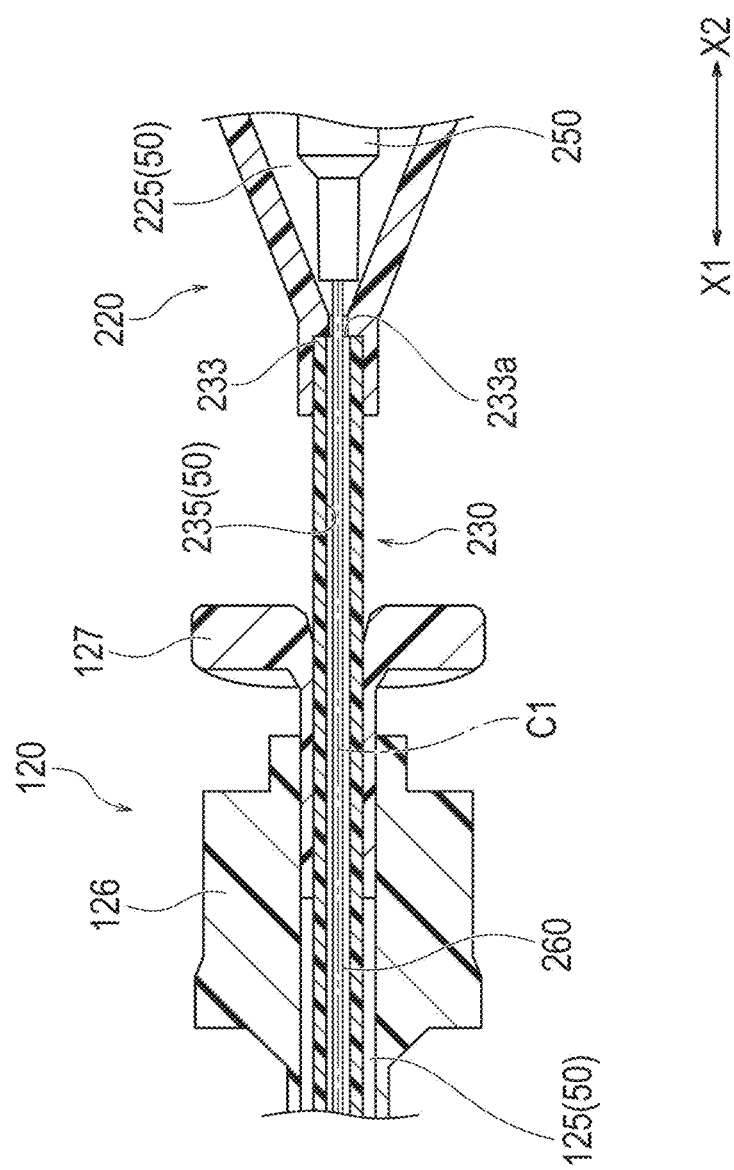
FIG. 3 is an enlarged cross-sectional view of a portion indicated as a dashed-line portion 3A in FIG. 1.

As illustrated in FIGS. 2 and 3, the first hub 120 includes: a distal cylindrical portion 121 that is located at the distal end portion; a hub main body 123 in which an internal space 125 communicating with the inside of the distal cylindrical portion 121 is provided; the port unit 124 that has a flow path communicating with the internal space 125 of the hub main body 123; and an opener 127 that is disposed on the proximal end side of the port unit 124.

The first hub 120 can be formed with a Y connector (a Y connector or the like with a valve mechanism that can be opened and closed by the opener 127, for example) that is known in the catheter field, for example.

A wing 130 can be disposed on the distal end side of the distal cylindrical portion 121 of the first hub 120. As the wing 130, one that is known in the catheter field can also be used like the Y connector. The proximal end portion 113 of the first shaft 110 is secured to the wing 130.

A proximal end opening 113a provided at the proximal end portion 113 of the first shaft 110 is disposed so as to communicate with an internal space 135 of the wing 130. The internal space 135 of the wing 130 communicates with the internal space 125 of the hub main body 123 via the distal cylindrical portion 121. Accordingly, when the contrast medium is supplied from the port unit 124 of the first hub 120, the contrast medium flows into the lumen 115 of the first shaft 110 via the port unit 124, the internal space 125 of the hub main body 123, the internal space 135 of the wing 130, and the proximal end opening 113a. The contrast medium that has flowed into the lumen 115 of the first shaft 110 is discharged to the outside of the first shaft 110 via the first opening 112a provided at the distal end portion 111 of the first shaft 110 and the plurality of second openings 112b.

As illustrated in FIG. 3, the opener 127 is disposed at a position on the proximal end side of a proximal end portion 126 of the hub main body 123. The second shaft 230 included in the energy application device 200 is inserted through the inside of the opener 127 and is inserted into the internal space 125 of the hub main body 123.

Figure 10:
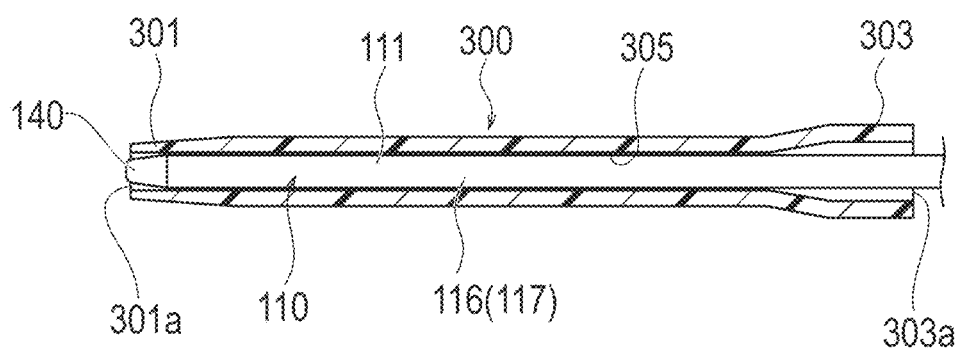
FIG. 10 is a cross-sectional view of an inserter included in the medical device.
Figure 11:
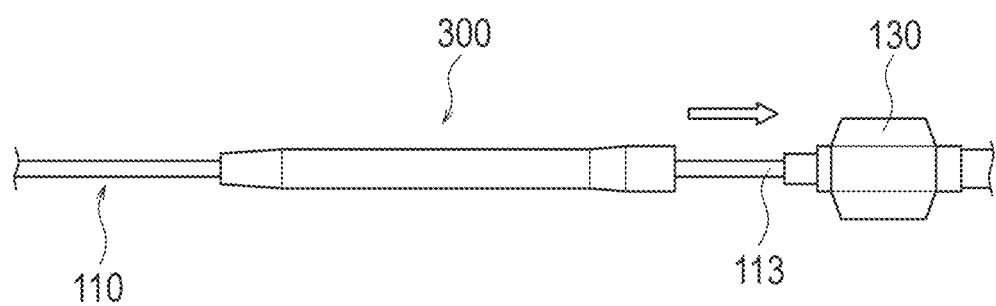
FIG. 11 is a view for explaining an example of use of the inserter included in the medical device.

As illustrated in FIGS. 1, 10, and 11, the medical device 10 can include a predetermined inserter 300.

The inserter 300 includes: a distal end opening 301a provided at a distal end portion 301; a proximal end opening 303a provided at a proximal end portion 303; and a lumen 305 that communicates with the distal end opening 301a and the proximal end opening 303b.

A tapered portion whose outer diameter and inner diameter become gradually smaller in the direction toward the distal end side is provided at the distal end portion 301 of the inserter 300. Also, a tapered portion whose outer diameter and inner diameter become gradually larger in the direction toward the proximal end side is provided at a position on the distal end side of the proximal end portion 303 of the inserter 300.

At the start of a procedure using the medical device 10, the inserter 300 is disposed near the distal end portion 111 of the first shaft 110 as illustrated in FIG. 10. As the inserter 300 is disposed near the distal end portion 111 of the first shaft 110, the shaped curved portion 116 (the spiral portion 117) of the first shaft 110 is straightened into a substantially linear shape along the inner surface shape of the inserter 300.

Before inserting the medical device 10 into the blood vessel V, the surgeon removes the energy application device 200 from the catheter device 100. In the state where the energy application device 200 has been removed from the catheter device 100, the surgeon uses the inserter 300 to correct the curved portion 116 of the first shaft 110 to have a substantially linear shape as described above. In the state where the curved portion 116 has been corrected to have a substantially linear shape, the surgeon inserts a guide wire over the entire length direction of the catheter device 100 via the first opening 112a of the first shaft 110, starting from the proximal end side of the guide wire inserted into the blood vessel V prior to the medical device 10. By moving the catheter device 100 along the guide wire, the surgeon can smoothly insert a certain range of the distal end portion 111 of the first shaft 110 of the catheter device 100 up to a predetermined position in the blood vessel V.

After inserting the certain range of the distal end portion 111 of the first shaft 110 into the blood vessel V in the above procedure, the surgeon removes the guide wire from the living body via the catheter device 100. After used for insertion of the medical device 10, the inserter 300 is moved along the outer surface of the first shaft 110 to the vicinity of the first hub 120, as illustrated in FIGS. 1 and 11. The inserter 300 can be configured to be connectable to the first hub 120, for example. The inserter 300 can be used as an anti-kink protector that protects the first shaft 110 by partially covering the first shaft 110 in a state of being connected to the first hub 120.

After removing the guide wire from the living body via the catheter device 100, the surgeon inserts the energy application device 200 from the first hub 120 of the catheter device 100. By moving the energy application device 200 along the first shaft 110 of the catheter device 100, the surgeon can place the energy application unit 210 at a predetermined position in the distal end portion 111 of the first shaft 110. Note that, using the opener 127, the surgeon can seal the portion between the first hub 120 and the second shaft 230 of the energy application device 200, to prevent leakage of liquid or the like to the proximal end side of the first hub 120.

The first shaft 110 has a structure that is shaped in advance so that the curved portion 116 (the spiral portion 117) is formed in at least part of the distal end portion 111 in a natural state where no external force is applied thereto. Accordingly, when the guide wire is removed from the first shaft 110, and the inserter 300 is moved to the proximal end side of the distal end portion 111, the curved portion 116 (the spiral portion 117) is restored to a predetermined curved shape, and at least a portion thereof is brought into contact with the inner wall Vi of the blood vessel V (see FIGS. 12 and 13).

<Energy Application Device 200>

As illustrated in FIG. 13, the energy application unit 210 is configured to be capable of emitting energy that can reach the surrounding nerve Na located outside the blood vessel V, in a state of being disposed in the lumen 115 of the first shaft 110.

The energy application unit 210 can be formed with an antenna element capable of emitting microwaves, for example. In a case where the energy application unit 210 is formed with an antenna element, the center frequency of the antenna element can be set to any of 915 MHz, 2.45 GHz, 5.8 GHz, and 24.125 GHz, for example.

The energy application unit 210 can also be formed with an ultrasonic element capable of emitting ultrasonic waves, for example. However, the energy application unit 210 is not limited to any particular structure, as long as the surrounding nerve Na extending in parallel with the outside the blood vessel V can be ablated. The energy application unit 210 can have a configuration capable of ablating the surrounding nerve Na, using a simple high frequency, a bipolar high frequency, high-density focusing ultrasonic waves, light, heat, cold radiation, an engineering therapy, a magnetic, electrical, or electromagnetic cryotherapy, plasma, mechanical energy, chemical energy, kinetic energy, potential energy, nuclear energy, or the like, for example.

Figure 4:
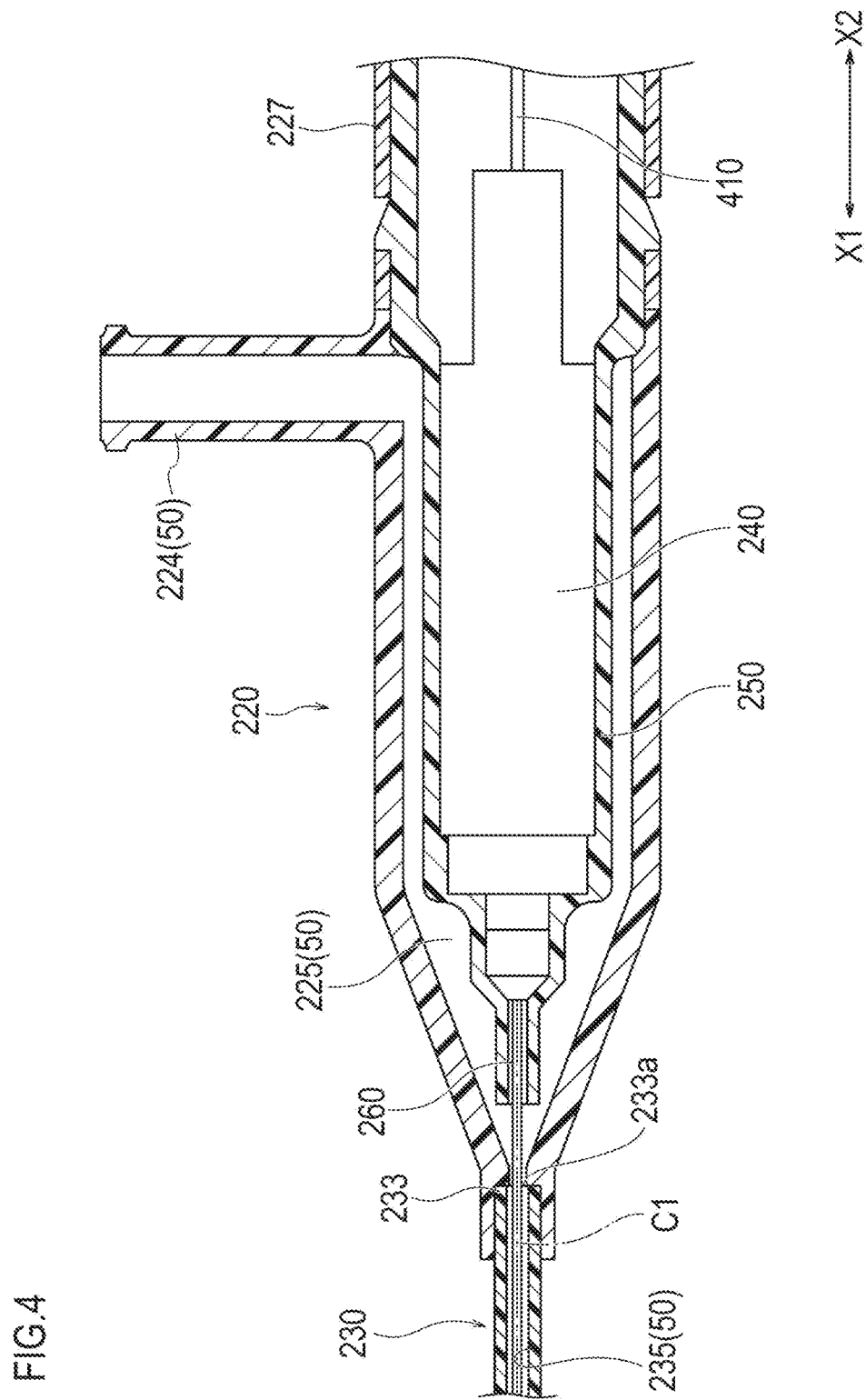
FIG. 4 is an enlarged cross-sectional view of a portion indicated as a dashed-line portion 4A in FIG. 1.

As illustrated in FIGS. 1 and 4, the second hub 220 of the energy application device 200 is disposed on the proximal end side of the first hub 120 of the catheter device 100.

The electrical connector unit 240 is accommodated in an internal space 225 of the second hub 220. The electrical connector unit 240 is covered with a predetermined housing 250.

The electrical connector unit 240 is configured to be connectable to a power supply unit 400, which is an external device, via a cord 410. Various electrical elements and the like for receiving power from the power supply unit 400 are disposed in the electrical connector unit 240.

The energy application unit 210 and the electrical connector unit 240 are connected via the conductive unit 260. The energy application unit 210 receives power from the electrical connector unit 240 via the conductive unit 260.

In a case where the energy application unit 210 is formed with an antenna element, the conductive unit 260 can be formed with a known coaxial cable capable of supplying current to the antenna element. Note that, in a case where the energy application unit 210 is formed with a component other than an antenna element, the conductive unit 260 can be formed with various electrical structural members that enable transmission of energy to the energy application unit 210.

As illustrated in FIGS. 1 and 4, an anti-kink protector 227 can be disposed at the proximal end portion of the second hub 220 of the energy application device 200.

As illustrated in FIG. 4, the internal space 225 of the second hub 220 communicates with the port unit 224. A clearance through which the perfusion liquid supplied from the port unit 224 can flow is provided between the electrical connector unit 240 accommodated in the internal space 225 of the second hub 220 and the inner surface of the second hub 220.

Note that, in the internal space 225 of the second hub 220, a portion closer to the proximal end side than the vicinity of the portion communicating with the port unit 224 is closed so that the perfusion liquid does not move closer to the proximal end side than the port unit 224.

A proximal end portion 233 of the second shaft 230 is connected to the distal end portion of the second hub 220. The internal space 225 of the second hub 220 communicates with a proximal end opening 233a provided in the proximal end portion 233 of the second shaft 230.

As illustrated in FIG. 2, the second shaft 230 extends from the second hub 220 to the distal end side, and its distal end portion 231 is disposed in the internal space 125 of the first hub 120.

The conductive unit 260 is inserted into the lumen 115 of the first shaft 110 via the internal space 225 of the second hub 220, the second shaft 230, the internal space 125 of the first hub 120, and the wing 130.

In the energy application device 200, the second shaft 230 can relatively move forward and backward with respect to the catheter device 100 so that the energy application unit 210 can be disposed at a predetermined position (a predetermined position of the curved portion 116, for example) on the distal end side of the first shaft 110.

An arrow f in FIGS. 1, 2, and 7 indicates a direction in which the energy application unit 210 and part of the second shaft 230 move forward along the lumen 115 of the first shaft 110. An arrow b indicates a direction in which the energy application unit 210 and part of the second shaft 230 move backward along the lumen 115 of the first shaft 110.

The surgeon grips the second hub 220 with fingers or the like, and causes the second hub 220 to slide forward and backward along a central axis C1 of the second shaft 230, so that the energy application device 200, together with the second hub 220, can relatively move forward and backward with respect to the catheter device 100.

The surgeon can selectively place the energy application unit 210 at any desired portion of the curved portion 116, by moving the energy application unit 210 along the curved portion 116 in a state where part of the curved portion 116 (the spiral portion 117) is in contact with the inner wall Vi of the blood vessel V as illustrated in FIGS. 12 and 13.

<Liquid Circulation Unit 50>

The liquid circulation unit 50 enables transfer of the perfusion liquid supplied from the port unit 224 of the second hub 220 to the distal end portion 111 of the first shaft 110.

Having the liquid circulation unit 50, the medical device 10 can cool the electrical connector unit 240 disposed in the internal space 225 of the second hub 220, the conductive unit 260 extending from the electrical connector unit 240 to the vicinity of the distal end portion 111 of the first shaft 110, and the energy application unit 210 disposed at the distal end of the conductive unit 260, with the perfusion liquid circulated via the liquid circulation unit 50. Accordingly, it is possible to prevent the occurrence of an excessive temperature rise in each of the units 240, 260, and 210 during treatment using the medical device 10.

As illustrated in FIGS. 2, 3, and 4, the liquid circulation unit 50 can be formed with a fluid communication passage that includes the port unit 224 of the second hub 220, the internal space 225 of the second hub 220, the lumen 235 of the second shaft 230, the internal space 125 of the first hub 120, and the lumen 115 of the first shaft 110. That is, the perfusion liquid supplied via the port unit 224 of the second hub 220 flows from the proximal end side to the distal end side in each of the portions 225, 235, 125, and 115, to cool the electrical connector unit 240, the conductive unit 260, and the energy application unit 210 in the course of flowing. The perfusion liquid that has flowed to the distal end portion 111 of the first shaft 110 is discharged to the outside of the first shaft 110 via the plurality of second openings 112b and the first opening 112a formed in the first shaft 110.

As illustrated in FIG. 2, the second shaft 230 is inserted into the first hub 120 so that the distal end portion 231 of the second shaft 230 becomes movable between a first position P1 defined in the first hub 120 and a second position P2 defined closer to the proximal end side in the first hub 120 than the first position P1. Note that specific positions of the first position P1 and the second position P2 are not limited to any particular positions, and can be set at any desired positions in the first hub 120.

In the medical device 10, the liquid circulation unit 50 is provided in both a state where the distal end portion 231 of the second shaft 230 is located at the first position P1 and a state where the distal end portion 231 is located at the second position P2.

Specifically, when the distal end portion 231 of the second shaft 230 is located at the first position P1, the distal end portion 231 of the second shaft 230 is in contact with the portion protruding toward the inner peripheral side of the distal cylindrical portion 121, and the first position P1 of the distal end portion 231 of the second shaft 230 is defined. In this state, the perfusion liquid can flow to the distal end side of the distal end portion 231 of the second shaft 230 via a distal end opening 231a of the second shaft 230. On the other hand, when the distal end portion 231 of the second shaft 230 is located at the second position P2, the perfusion liquid can flow toward the distal end side of the distal end portion 231 of the second shaft 230 via the distal end opening 231a of the second shaft 230 and the internal space 125 of the hub main body 123.

As described above, the medical device 10 according to the present embodiment includes: the catheter device 100 that includes: the first shaft 110 that is configured to be insertable into the blood vessel V and has one or more openings 112a and 112b formed at the distal end portion 111; and the first hub 120 disposed at the proximal end portion 113 of the first shaft 110; the energy application device 200 that includes: the energy application unit 210 that is configured to be capable of applying energy to the surrounding nerve Na extending in parallel with the blood vessel V, to ablate the surrounding nerve Na outside the blood vessel V; the second hub 220 in which the electrical connector unit 240 for supplying electrical energy to the energy application unit 210 is disposed, the second hub 220 including the port unit 224 that supplies a predetermined liquid to the inside of the second hub 220; the elongated conductive unit 260 that connects the electrical connector unit 240 and the energy application unit 210; and the second shaft 230 that extends from the second hub 220 toward the energy application unit 210, accommodates at least part of the proximal end side of the conductive unit 260, and is inserted into the first hub 120; and the liquid circulation unit 50 that enables transfer of the liquid supplied from the port unit 224 to the distal end portion 111 of the first shaft 110, in which the energy application device 200 is capable of relatively moving forward and backward with respect to the catheter device 100 so that the energy application unit 210 can be disposed at a predetermined position on the distal end side of the first shaft 110.

With the medical device 10, it is possible to ablate, outside the blood vessel V, the surrounding nerve Na extending in parallel with the blood vessel V, by causing energy emission from the energy application unit 210 disposed in the first shaft 110 of the catheter device 100. Also, the medical device 10 includes the liquid circulation unit 50 that enables transfer of the liquid (perfusion liquid) supplied from the port unit 224 of the second hub 220 of the energy application device 200 to the distal end portion 111 of the first shaft 110. Thus, during treatment, the surgeon can cool the energy application unit 210 and the conductive unit 260 disposed in the first shaft 110 of the catheter device 100 with the perfusion liquid.

Although a medical device according to the present invention has been described so far through an embodiment, the present invention is not limited only to the details described in the specification, and can be appropriately changed on the basis of the disclosure in the claims.

In the above-described embodiment, the superior mesenteric artery Va has been described as an example of the blood vessel V to be treated by the medical device 10. However, the blood vessel V to be treated by the medical device is not limited to any particular kind. For example, it is possible to select a pulmonary vein as the blood vessel to be treated. By locally applying energy to the surrounding nerves running outside the pulmonary artery and performing ablation, it is possible to treat a disease such as atrial fibrillation and facilitate recovery.

Also, in the medical device, any component or the like not specifically described in the specification can be added as appropriate, and the additional members described in the specification can be omitted as appropriate. Further, as for the treatment using the medical device, any procedure not specifically described in the specification can be added as appropriate, and the additional procedures described in the specification can be omitted as appropriate. Furthermore, in the treatment method, the sequence of procedures can be changed as appropriate, as long as the effects of the invention can be achieved.

REFERENCE SIGNS LIST

10 Medical device
50 Liquid circulation unit
100 Catheter device
110 First shaft
111 Distal end portion of the first shaft
112a First opening
112b Second opening
113 Proximal end portion of the first shaft
113a Proximal end opening of the first shaft
115 Lumen of the first shaft
116 Curved portion
117 Spiral portion
118 Linear portion
119a First portion
119b Second portion
119c Third portion
120 First hub
121 Distal cylindrical portion
123 Hub main body
124 Port unit of the first hub
125 Internal space of the hub main body
200 Energy application device
210 Energy application unit
220 Second hub
224 Port unit of the second hub
225 Internal space of the second hub
230 Second shaft
231 Distal end portion of the second shaft
231a Distal end opening of the second shaft
233 Proximal end portion of the second shaft
233a Proximal end opening of the second shaft
235 Lumen of the second shaft
240 Electrical connector unit
260 Conductive unit
300 Inserter
400 Power supply unit
A1 First reference axis
A2 Second reference axis
C1 Central axis of the second shaft
Na Surrounding nerve
OA Center position of a blood vessel
P1 First position
P2 Second position
S Treatment target site
V Blood vessel
Vi Inner wall of the blood vessel
Va Superior mesenteric artery

The invention claimed is:

1. A medical device comprising:
a catheter device that includes:
a first shaft that is configured to be insertable into a blood vessel and has one or more openings formed at a distal end portion; and
a first hub disposed at a proximal end portion of the first shaft;
an energy application device that includes:
an energy application unit configured to apply energy to a surrounding nerve outside the blood vessel, the energy being for ablating the surrounding nerve running in parallel with the blood vessel;
a second hub in which an electrical connector unit that supplies electrical energy to the energy application unit is disposed, the second hub including a port unit for inwardly supplying a predetermined liquid;
a conductive unit that has an elongated shape and connects the electrical connector unit and the energy application unit; and
a second shaft that extends from the second hub to a side of the energy application unit, accommodates at least part of a proximal end side of the conductive unit, and is inserted into the first hub; and
a liquid circulation unit that allows the liquid supplied from the port unit to be sent to the distal end portion of the first shaft, wherein
the energy application device is relatively movable forward and backward with respect to the catheter device, so that the energy application unit can be placed at a predetermined position on a distal end side of the first shaft,
the liquid circulation unit is a fluid communication passage that includes the port unit of the second hub, an internal space of the second hub, a lumen of the second shaft, an internal space disposed immediately inside the first hub, and a lumen of the first shaft, wherein these components are in serial communication, and
the liquid circulation unit includes a clearance around the electrical connector unit in the internal space of the second hub.

2. The medical device according to claim 1, wherein
the second shaft is inserted into the first hub, to allow a distal end portion of the second shaft to move between a first position defined in the first hub and a second position defined closer to a proximal end side in the first hub than the first position, and
the liquid circulation unit is provided in both a state where the distal end portion of the second shaft is located at the first position and a state where the distal end portion of the second shaft is located at the second position.

3. The medical device according to claim 1, wherein the one or more openings include:
- a first opening formed at a distal end of the first shaft; and
- a plurality of second openings that is located on a proximal end side of the first opening and is open toward a lateral side of the first shaft.

4. The medical device according to claim 3, wherein the plurality of second openings is open in a direction not to face an inner wall of the blood vessel in a state where the first shaft is inserted in the blood vessel.

5. The medical device according to claim 4, wherein the distal end portion of the first shaft includes:
- a curved portion that has a shape curved with respect to a predetermined first reference axis; and
- a linear portion that is located on a proximal end side of the curved portion, and extends substantially linearly along a second reference axis extending in a direction intersecting with the first reference axis.

6. The medical device according to claim 5, wherein the curved portion is a spiral portion that extends spirally around the first reference axis.

7. The medical device according to claim 5, wherein the first shaft includes:
- a first portion included in the curved portion;
- a second portion that is located on a proximal end side of the first portion, wherein the plurality of second openings are formed in the second portion; and
- a third portion that is located on a proximal end side of the second portion, and is included in the linear portion, and
- an inner diameter of the second portion and the third portion is larger than an inner diameter of the first portion.

8. The medical device according to claim 1, wherein the energy application unit is capable of emitting a microwave or an ultrasonic wave as the energy.

* * * * *